(12) United States Patent
Wakashiro

(10) Patent No.: US 7,522,209 B2
(45) Date of Patent: Apr. 21, 2009

(54) AUTOMATIC FOCUSING APPARATUS INCLUDING OPTICAL FLOW DEVICE CALCULATION

(75) Inventor: Shigeru Wakashiro, Tokyo (JP)

(73) Assignee: Hoya Corporation, Tokyo (JP)

( * ) Notice: Subject to any disclaimer, the term of this patent is extended or adjusted under 35 U.S.C. 154(b) by 1019 days.

(21) Appl. No.: 10/740,758

(22) Filed: Dec. 22, 2003

(65) Prior Publication Data

US 2004/0130651 A1    Jul. 8, 2004

(30) Foreign Application Priority Data

Dec. 26, 2002 (JP) ............... 2002-377547
Dec. 26, 2002 (JP) ............... 2002-377548

(51) Int. Cl.
H04N 5/232 (2006.01)
G03B 13/00 (2006.01)
A62B 1/04 (2006.01)
H04N 7/18 (2006.01)
H04N 9/47 (2006.01)

(52) U.S. Cl. .................. 348/345; 348/349; 348/356; 348/65

(58) Field of Classification Search ............. 348/345, 348/349, 354, 356, 65
See application file for complete search history.

(56) References Cited

U.S. PATENT DOCUMENTS

| | | | |
|---|---|---|---|
| 5,012,270 A | 4/1991 | Sekine et al. | |
| 5,315,339 A | 5/1994 | Hamada et al. | |
| 5,386,264 A | 1/1995 | Sekine et al. | |
| 5,448,329 A | 9/1995 | Nakata | |
| 5,612,761 A | 3/1997 | Nakata | |
| 5,613,166 A | 3/1997 | Hamada et al. | |
| 5,724,619 A | 3/1998 | Hamada et al. | |
| 5,734,933 A | 3/1998 | Sekine et al. | |
| 5,896,174 A | 4/1999 | Nakata | |
| 5,949,481 A * | 9/1999 | Sekine et al. | .......... 348/207.99 |
| 6,047,134 A | 4/2000 | Sekine et al. | |

(Continued)

FOREIGN PATENT DOCUMENTS

JP    1-194684    8/1989

(Continued)

OTHER PUBLICATIONS

Jo, G. et al. "Three-Dimensional Vision," Kyoritsu Shuppan, pp. 111-118, together with an English language translation.

(Continued)

*Primary Examiner*—Ngoc-Yen T Vu
*Assistant Examiner*—Kelly L Jerabek
(74) *Attorney, Agent, or Firm*—Greenblum & Bernstein, P.L.C.

(57) ABSTRACT

An automatic focusing apparatus includes an image pickup optical system; an image pickup device for converting an optical image formed by the image pickup optical system into an electric image signal at a predetermined cycle and outputting the electric signal; a focusing device; an optical flow calculation device for calculating optical flows in accordance with the image signals in a first image plane at a first time and a second image plane at a second time different from the first time, and for calculating an average of magnitudes and directions of the optical flows; and a judgment device for determining whether or not the focusing device is to be driven in accordance with calculated average of the magnitudes and the directions of the optical flows.

9 Claims, 10 Drawing Sheets

U.S. PATENT DOCUMENTS

| | | |
|---|---|---|
| 6,241,656 B1 | 6/2001 | Suga |
| 6,370,330 B2 | 4/2002 | Sekine et al. |
| 6,665,450 B1 * | 12/2003 | Cornog et al. .............. 382/276 |
| 2002/0012063 A1 * | 1/2002 | Kobayashi .................. 348/345 |

FOREIGN PATENT DOCUMENTS

| | | |
|---|---|---|
| JP | 2-205810 | 8/1990 |
| JP | 4-346303 A | 12/1992 |
| JP | 5-7325 | 1/1993 |
| JP | 2000-005127 | 1/2000 |
| JP | 2000-197604 | 7/2000 |
| JP | 2000-342533 | 12/2000 |
| JP | 2001-033710 | 2/2001 |
| JP | 2001-154085 | 6/2001 |

OTHER PUBLICATIONS

English language Abstract of JP 2-205810, (Aug. 1990).
English language Abstract of JP 1-194684, (Aug. 1989).
English language Abstract of JP 5-7325, (Jan. 1993).
English language Abstract of JP 4-346303 A, Dec. 2, 1992.

* cited by examiner

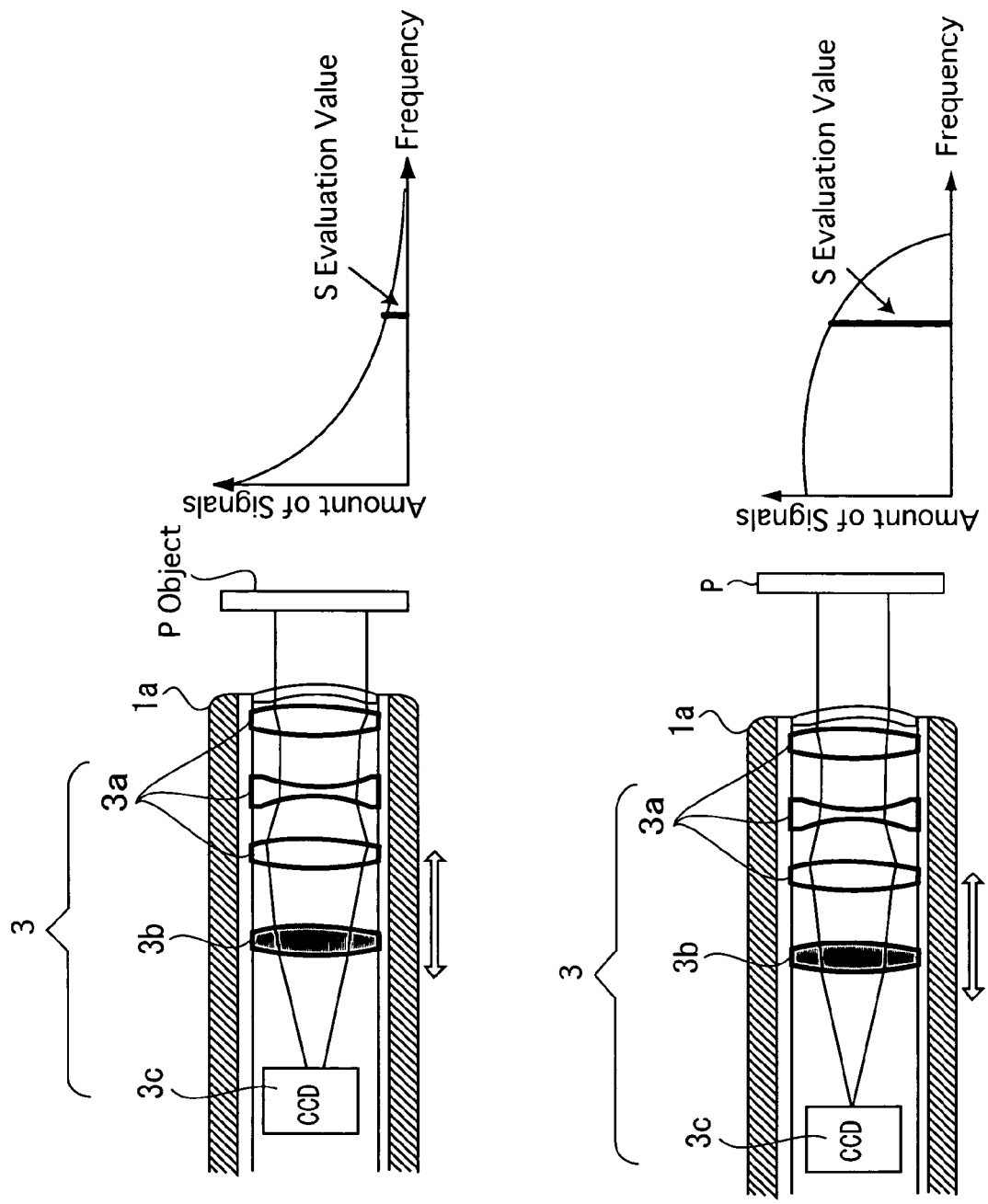

AUTOMATIC FOCUSING APPARATUS INCLUDING OPTICAL FLOW DEVICE CALCULATION

BACKGROUND OF THE INVENTION

1. Field of the Invention

The present invention relates to an automatic focusing apparatus which is particularly suitable for an electronic endoscope.

2. Description of the Related Art

In recent years, an electronic endoscope having an automatic focusing apparatus has been developed. In a conventional automatic focusing apparatus, focus detection is carried out in such a way that when the evaluation value of the high frequency component of an image signal picked up by a CCD-type or CMOS-type image pickup device becomes maximum, i.e., when a high frequency component for a contour portion of an object image becomes maximum, it is deemed that the image is in focus. During a diagnosis using an electronic endoscope, as the object to be detected frequently changes in accordance with the endoscopic operation, hunting of the automatic focusing optical system occurs if the automatic focusing apparatus is continuously activated. Alternatively, in order to activate the automatic focusing apparatus only when automatic focusing is necessary, a separate switch must be provided to activate the automatic focusing apparatus. However, such a switch must be operated each time the automatic focusing apparatus is activated or deactivated.

An electronic endoscope having an automatic focusing apparatus is disclosed, for example, in References No. 1 through No. 4 below.

Reference No. 1: Japanese Kokai (Unexamined Patent Publication) No. 2001-154085

Reference No. 2: Japanese Kokai (Unexamined Patent Publication) No. 2000-5127

Reference No. 3: Japanese Kokai (Unexamined Patent Publication) No. 2000-197604

Reference No. 4: Japanese Kokai (Unexamined Patent Publication) No. 2000-342533

SUMMARY OF THE INVENTION

The present invention eliminates the drawbacks of the prior art mentioned above by providing an automatic focusing apparatus, in which during use of an electronic endoscope, an automatic focusing operation is carried out only if required, without providing an ON/OFF switch for the automatic focusing operation.

According to an aspect of the present invention, an automatic focusing apparatus is provided, including an image pickup optical system; an image pickup device for converting an optical image formed by the image pickup optical system into an electric image signal at a predetermined cycle and outputting the electric signal; a focusing device; an optical flow calculation device for calculating optical flows in accordance with the image signals in a first image plane at a first time and a second image plane at a second time different from the first time, and for calculating an average of magnitudes and directions of the optical flows; and a judgment device for determining whether or not the focusing device is to be driven in accordance with calculated average of the magnitudes and the directions of the optical flows. With this structure, since whether the object distance is reduced or increased is determined in accordance with the optical flows which are obtained from the picked-up image signals, the focusing device is driven to obtain a clear object image which is in focus only when it is necessary.

It is desirable for a signal separating device to be provided for separating luminance signals from image signals supplied by the image pickup device, wherein the optical flow calculation device calculates optical flows in accordance with the luminance signals.

The optical flow calculation device can detect a plurality of characteristic points, based on the luminance signals of the first image plane and the second image plane, and calculates the optical flows based on the characteristic points in the first image plane and the characteristic points in the second image plane.

The judgment device can determine that the focusing device is not driven when the optical flow calculation device fails to calculate the average of the magnitude and the direction of each optical flow.

It is desirable for the image pickup optical system to include a focusing optical system which is moved along an optical axis to perform a focusing operation, and wherein the focusing device includes a drive device for moving the focusing optical system and a focus detection device for detecting a focus state in accordance with the image signals output from the image pickup device.

The automatic focusing apparatus can further include a power varying device for varying the optical power of the focusing optical system by moving the focusing optical system in the optical axis direction.

It is desirable for the focus detection device to detect the focus state by detecting a contrast based on the image signals.

It is desirable for the focusing optical system to be normally located in a pan-focus position and the judgment device activates the focusing device when the average of the magnitudes of the optical flows is below a predetermined value.

It is desirable for the optical flow calculation device to weight the magnitudes of the optical flows in accordance with the position of the focusing optical system in the optical axis direction.

In another embodiment, an automatic focusing apparatus is provided, including an image pickup optical system; an image pickup device for converting an optical image formed by the image pickup optical system into an electric image signal at a predetermined cycle and outputting the electric signal; a focusing device; a calculation device for calculating optical flows in accordance with the image signals in a first image plane at a first time and a second image plane at a second time different from the first time; and a control device for driving the focusing device in a direction toward a focus for a short object distance when the optical flows diverge and for driving the focusing device in a direction toward a focus for a long object distance when the optical flows converge.

With this arrangement, when the object distance is reduced, the optical flows diverge. Consequently, the focusing device is driven in a direction toward the focus position for a short object distance. When the object distance is increased, the optical flows converge. Consequently, the focusing device is driven in a direction toward the focus position for a long object distance. Thus, the focusing device can be driven in a correct direction in accordance with an increase or decrease of the object distance.

It is desirable for a signal separating device to be provided for separating luminance signals from the image signals supplied by the image pickup device, wherein the optical flow calculation device calculates optical flows in accordance with the luminance signals.

It is desirable for the calculation device to calculates an average of the magnitudes and the directions of the calculated optical flows.

It is desirable for the control device to hold the focusing device in a current state when the optical flows neither diverge nor converge and are below a predetermined value.

It is desirable for the image pickup optical system to include a focusing optical system which is moved along an optical axis to control the focus, and for the focusing device to include a drive device for moving the focusing optical system and a focus detection device for detecting the focus state in accordance with the image signals output from the image pickup device.

The present disclosure relates to subject matter contained in Japanese Patent Application Nos. 2002-377547 and 2002-377548 (filed on Dec. 26, 2002) which are expressly incorporated herein by reference in their entireties.

BRIEF DESCRIPTION OF THE DRAWINGS

The invention will be discussed below with reference to the accompanying drawings, in which:

FIG. 3A is a schematic view showing a relationship between an image pickup device and an image pickup optical system in a rear focus position;

FIG. 3B is a schematic view showing a relationship between an image pickup device and an image pickup optical system in an in-focus position;

DESCRIPTION OF THE PREFERRED EMBODIMENTS

Figure 1:
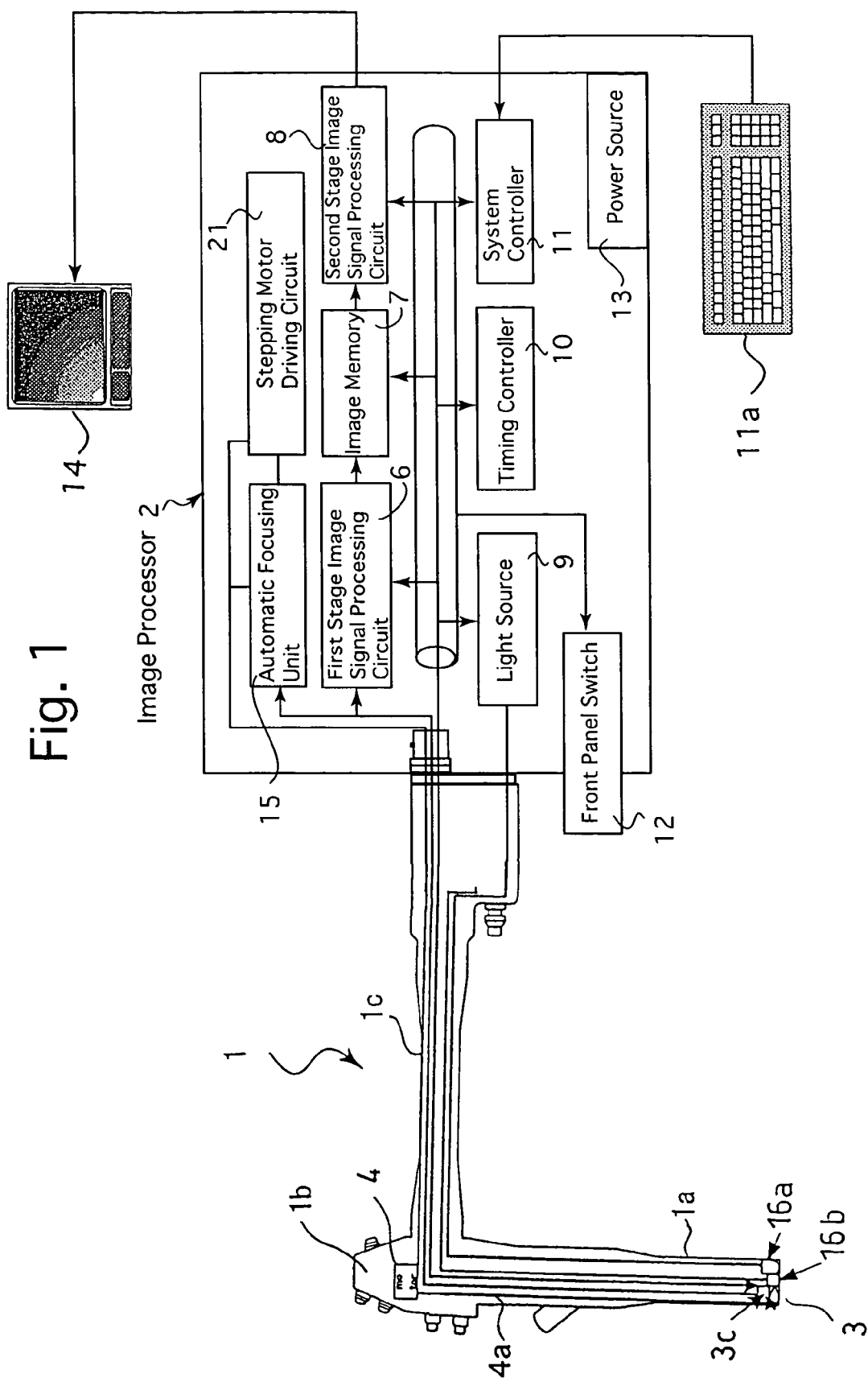
FIG. 1 is a block diagram of an electronic endoscope having an automatic focusing apparatus according to an embodiment of the present invention.

The invention will be discussed with reference to the drawings. FIG. 1 is a block diagram of an embodiment of an electronic endoscope having an automatic focusing apparatus according to the present invention.

An electronic endoscope is constructed from a combination of an endoscope 1 which forms an image of an object on an image pickup surface of an image pickup device 3c through a photographing optical system 3 and converts the object image into an electric image signal, and an image processor 2 which processes the image signal and controls the entire apparatus.

The endoscope 1 is comprised of an elongated flexible insertion tube 1a which can be inserted in a patient's body cavity, an operating portion 1b which is provided at an external end of the insertion tube 1a, and a cable connector 1c which can be connected to an image processor 2. The image pickup optical system 3 and the image pickup device 3c are incorporated in the insertion tube 1a at the front end of the tube to be inserted in the body cavity.

As can be seen in FIGS. 2 and 3A through 3C, the image pickup optical system 3 is constructed from a stationary lens system 3a provided at a fixed position, a movable lens system 3b which can be moved away from or close to the stationary lens system 3a, and the image pickup device 3c which is movable relative to the stationary lens system 3a and the movable lens system 3b and which converts an optical image formed through the stationary lens system 3a and the movable lens system 3b into an electric signal.

In this embodiment, the focal length is varied (i.e., the optical power is varied) mainly by moving the image pickup device 3c along the optical axis, and focusing is carried out mainly by moving the movable lens system 3b along the optical axis. The relative displacement area of the movable lens system 3b and the image pickup device 3c is divided into two areas: a short focal length area and a long focal length area. Focusing is carried out by the relative movement of the movable lens system 3b and the image pickup device 3c to move away from or close to each other in each area.

Figure 2:
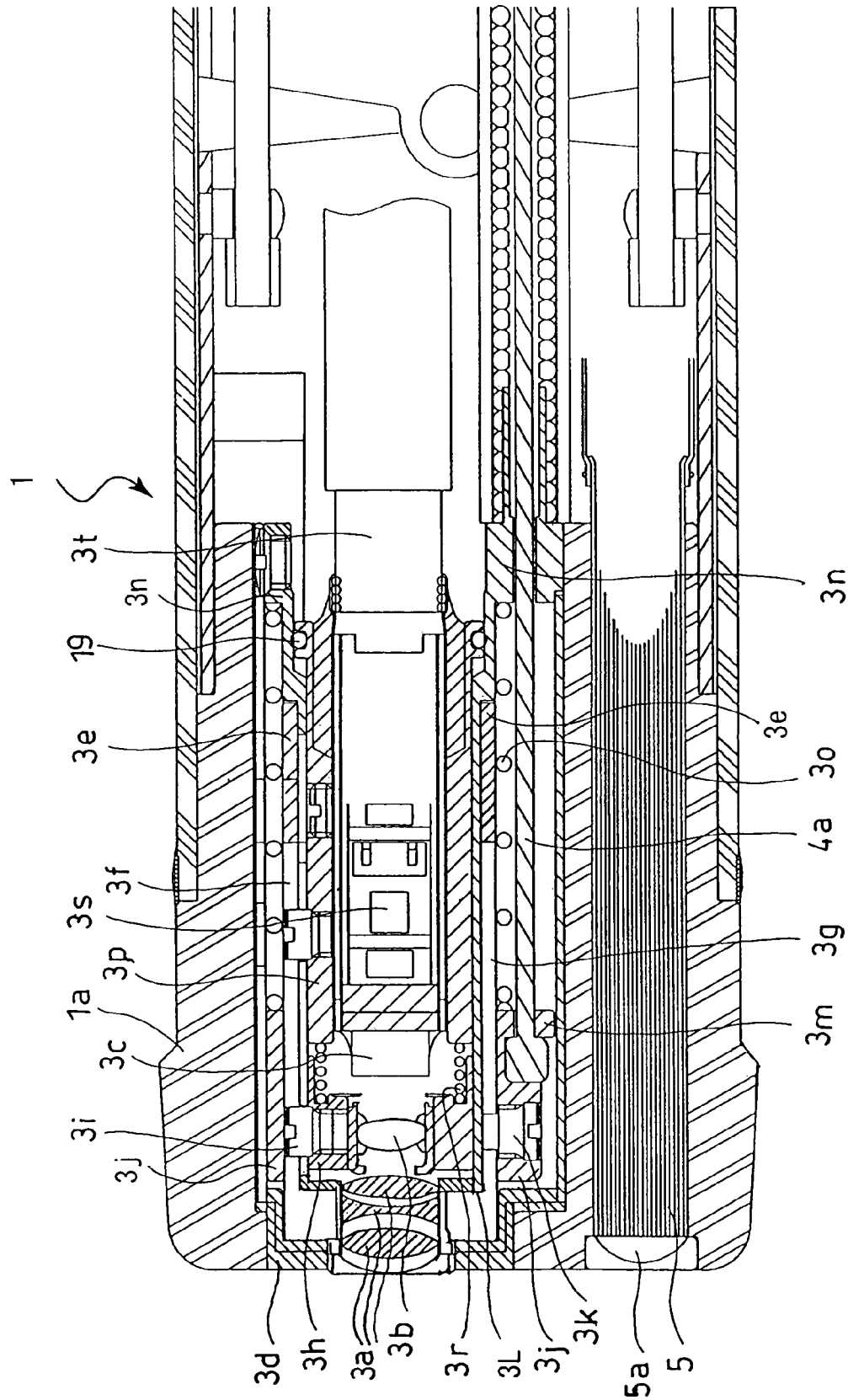
FIG. 2 is a longitudinal sectional view of an insertion tube to show a relationship between an image pickup device and an image pickup optical system, at a front end of the insertion tube of an electronic endoscope, according to the present invention.

An example of the image pickup optical system 3 having a vari-focal lens function will be discussed with reference to FIGS. 2 and 3A to 3C. As can be seen in FIG. 2, a cylindrical stationary lens frame 3d is provided in the front end of the insertion tube 1a of the endoscope 1, so that the stationary lens 3a of the image pickup optical system 3 is secured to the stationary lens frame 3d. A cylindrical guide frame 3e is provided with linear guide grooves 3f and 3g in parallel with the optical axis (right and left direction in FIG. 2), and is provided in the stationary lens frame 3d.

A movable lens frame 3h is fitted in the guide frame 3e so as to move in the optical axis direction. The movable lens frame 3h can be linearly moved in the optical axis direction without rotating about the optical axis by fitting a key 3i of the movable lens frame 3h in the linear guide groove 3f (i.e., the upper guide groove in FIG. 2) of the guide frame 3e. A ring 3j is fitted on the guide frame 3e and is connected to the movable lens frame 3h by a screw 3k which extends through the linear guide groove 3g (i.e., the lower guide groove in FIG. 2) of the guide frame 3e. A spring seat 3n is provided at the rear end of the guide frame 3e. A cylindrical member 3L is provided between the image pickup device frame 3p and the guide frame 3e and is provided at its rear end with a spring seat 3n. The cylindrical member 3L is provided with a slit (not shown) which permits the screw 3k to move in the optical axis direction.

The ring 3j is provided with a flange 3m which is associated with a stepping motor 4 shown in FIG. 1 through a connecting member 4a, so that the movable lens frame 3h can be linearly moved in the optical axis direction by the stepping motor 4. The movable lens system 3b is mounted to the movable lens frame 3h and is adjacent to the stationary lens system 3a, so that when the movable lens frame 3h is linearly moved, the distance between the stationary lens system 3a and the movable lens system 3b is varied. In this embodiment, focusing is carried out by varying the distance between the stationary lens system 3a and the movable lens system 3b.

A spring 3o is provided between the ring 3j and the spring seat 3n to bias the movable lens frame 3h in a direction to move the movable lens frame 3h close to the movable lens system 3b. The spring 3o continuously biases the movable lens frame 3h toward the stationary lens system 3a, so that when the force applied to the movable lens frame 3h by the stepping motor 4 is released, the movable lens frame 3h is moved toward the stationary lens system 3a to thereby return the movable lens system 3b to a predetermined initial position. The initial position corresponds to the longest focal position and to the pan-focus position.

The image pickup device frame 3p is fitted in the guide frame 3e. The image pickup device 3c is mounted to the image pickup device frame 3p and is adjacent to the movable lens system 3b. A spring 3r is provided between the image pickup device frame 3p and the movable lens frame 3h to bias the movable lens system 3b in a direction away from the image pickup device 3c to thereby prevent the movable lens system 3b from coming into contact with the light receiving surface of the image pickup device 3c. Numeral 19 designates the seal member in the form of an O-ring.

The image pickup device frame 3p is provided with a circuit mounted thereto, such as an image pickup device driving circuit 3s which drives and controls the image pickup device 3c which converts the object image formed by the image pickup optical system 3 into an electric signal and outputs the electric signal, and a signal cable 3t which transmits the electric signal supplied from the image pickup device 3c, etc. The bi-directional signal cable 3t transmits the electrical image signal supplied from the image pickup device 3c to a first stage image signal processing circuit 6 and transmits the signal processed in the first stage image signal processing circuit 6 to the image pickup device drive circuit 3s, etc. The bi-directional signal transmission is controlled by a timing controller 10.

A light passage 5 is provided in the insertion tube 1a adjacent to the image pickup optical system 3. The light passage 5 serves as a light guide through which illumination light emitted from a light source 9 to the insertion tube 1a. The light is irradiated onto the object through the lens 5a at the front end of the insertion tube 1a. The diameter of the insertion tube 1a which is inserted in the body cavity must be small, and to this end, the light passage 5 is preferably made of an optical fiber bundle.

As shown in FIG. 1, the image processor 2 includes the first stage image signal processing circuit 6, an image memory 7, a second stage image signal processing circuit (signal separating device/optical flow calculation device) 8, the light source 9, the timing controller 10, a system controller (judgment device/control device) 11, a front panel switch 12, and an electrical power source 13.

The first stage image signal processing circuit 6 processes the electric signal transmitted from the image pickup device 3c through the signal cable 3t. The processed image signals are successively stored in the image memory 7. The second stage image processing circuit 8 successively reads and processes the image signals accumulated in the image memory 7 and outputs the image signals to the monitor 14. The monitor 14 displays the image signal output from the second stage image signal processing circuit 8 as a visible image on a display surface.

The system controller 11 generally controls the image processor 2 in accordance with instruction data input through a keyboard 11a and a program stored in a memory (not shown). The timing controller 10 controls the timing of the operations of each block of the image processor 2, based on the instructions from the system controller 11. The image processor 2 is supplied with electricity from the power supply source 13.

The light source 9 emits light to the light passage 5 through a diaphragm whose aperture is controlled in accordance with a light quantity control signal which is obtained by detecting the brightness of the picked-up image in accordance with the electric signal supplied from the image pickup device 3c through the signal cable 3t.

An automatic focusing unit (focusing device/focus detection device) 15 includes an in-focus state detection circuit which detects that the image is in-focus, so that the stepping motor (drive device) 4 can be driven and controlled by a stepping motor drive circuit 21, in accordance with the in-focus state detected by the in-focus state detection circuit. The stepping motor drive circuit 21 drives the stepping motor 4 to thereby move the movable lens system 3b within the variable focus control range of the image pickup optical system 3.

The in-focus state detection circuit of the automatic focusing unit 15 detects the evaluation value in accordance with the image signal output from the image pickup device 3c. As can be understood in FIGS. 3A and 3C, if the object image formed by the image pickup optical system 3 is out of focus, the automatic focusing unit 15 rotates the stepping motor 4 through the stepping motor drive circuit 21 in the clockwise direction or counterclockwise direction, to thereby move the movable lens system 3b forward or backward. The movable lens system 3b is stopped when the image is in focus. The focusing is carried out by controlling the relative position of the movable lens system 3b, the stationary lens system 3a and the image pickup device 3c (FIG. 3B).

The automatic focusing unit 15 carries out the focusing operation of the image pickup optical system 3 based on the evaluation value of a predetermined frequency component included in the signal output from the image pickup device 3c. Specifically, the automatic focusing unit 15 controls the focal position, based on the evaluation value S of the high frequency component (included in the signal from the image pickup device 3c) which is increased or reduced in accordance with the focus state of the image pickup optical system 3, as shown in FIGS. 3A to 3C.

Figure 3C:
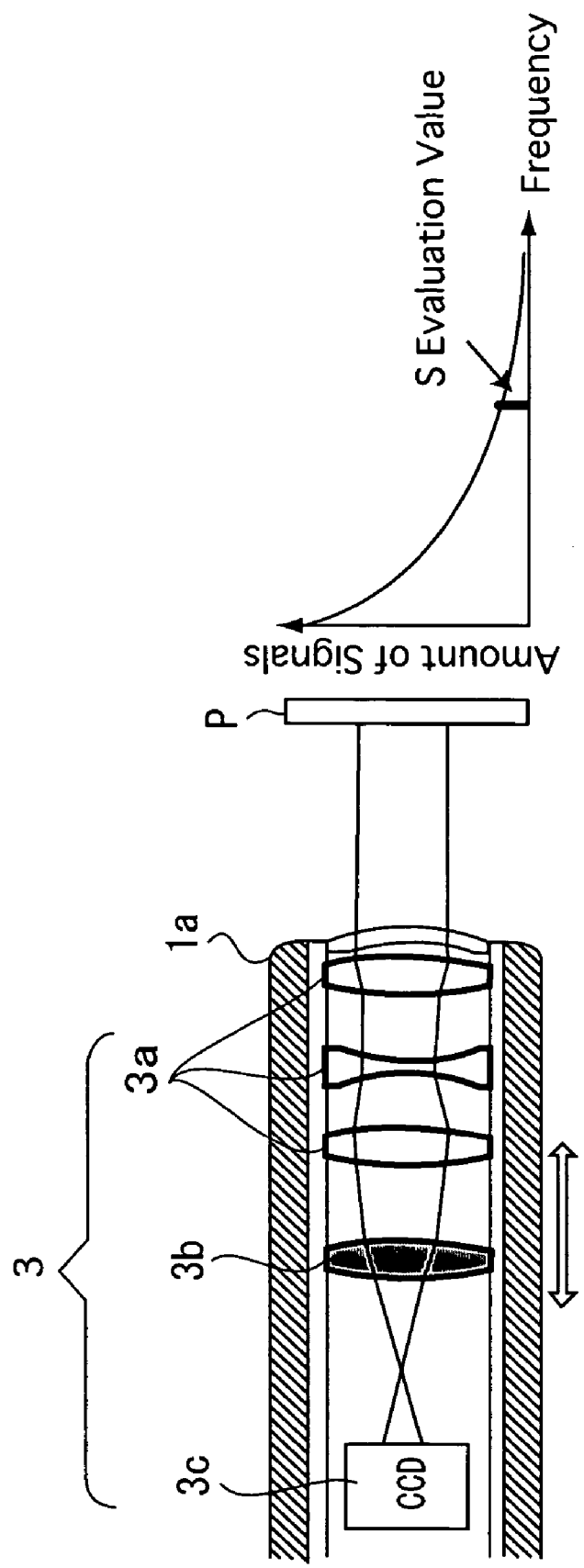
FIG. 3C is a schematic view showing a relationship between an image pickup device and an image pickup optical system in a front focus position.

When the movable lens system 3b is moved from the rear focus position shown in FIG. 3A by the automatic focusing unit 15 so that the focal point of the image pickup optical system 3 is identical to the light receiving surface of the image pickup device 3c, the high frequency component of the signal output from the image pickup device 3c is increased as shown in FIG. 3B. When the focal point of the image pickup optical system 3 is located in front of the image pickup device 3c (rear focus), the high frequency component of the signal output from the image pickup device 3c is reduced, as shown in FIG. 3C.

The automatic focusing unit 15 detects the focus state based on an increase or decrease of the high frequency component included in the signal output from the image pickup device 3c depending on the focus state of the image pickup optical system 3. When the high frequency component is maximum, the evaluation value is maximum, which indicates that the object is in-focus.

When the object distance is varied with respect to the focus state shown in FIG. 3B, a focal position shown in FIG. 3A or 3C is obtained. However, in such a focal position, it is impossible to determine whether the object has moved away from or close to the apparatus only by the detection of the increase or decrease of the high frequency component.

Accordingly, in the first embodiment of the invention, a plurality of characteristic points (luminance signals) are extracted (separated) from the image signal output from the image pickup device 3c. The optical flows for the characteristic points are calculated and summed up and the directions are totalized. If no characteristic point is extracted, for example, if almost no contrast exists or the movement is too quick to obtain characteristic points, it is impossible to calculate the optical flows. In this case, it is impossible to perform the focusing operation by activating the focusing device. Furthermore, there is a possibility of hunting occurring. To prevent this, if no optical flow can be calculated, the automatic focusing operation is not carried out according to one of the features of the illustrated embodiment.

In a second embodiment of the present invention, optical flows for a plurality of characteristic points are obtained based on the image signal output from the image pickup device 3c. The direction of the optical flows, i.e., whether the optical flows converge or diverge or do not converge nor diverge, are determined. If the optical flows diverge, it is judged that the object is closer, and if the optical flows converge, it is judged that the object is farther away from the apparatus. Based on this judgment, the direction of the focus adjustment is determined. The automatic focusing operation is carried out only when the convergence or divergence of the optical flows is detected and the amount thereof is above a predetermined value.

The focus detecting structure of the automatic focusing apparatus according to a first embodiment of the present invention will be explained below. In this embodiment, the image pickup optical system 3 carries out the image pickup operation while normally maintaining the image pickup optical system 3 in a pan-focus state to measure the optical flows of the characteristic points based on the picked-up image. If the optical flows of the characteristic points converge or diverge, the automatic focusing operation is carried out in accordance with the direction of the convergence or divergence and the amount thereof. The pan-focus state in this embodiment corresponds to the longest focal length at which the movable lens system 3b is positioned at a most advanced position.

Figure 4B:
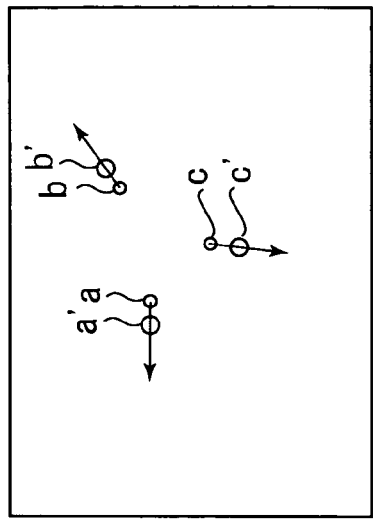
FIG. 4B is a schematic view showing three diverging characteristic points.
Figure 4D:
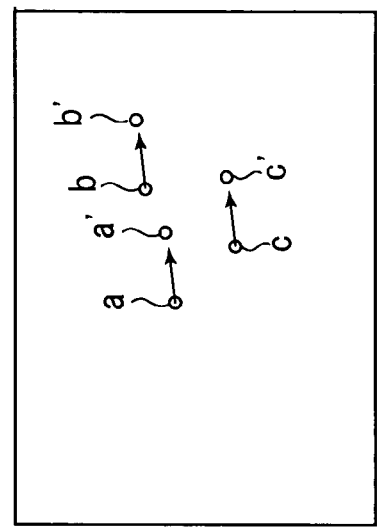
FIG. 4D is a schematic view showing three shifting characteristic points.
Figure 4A:
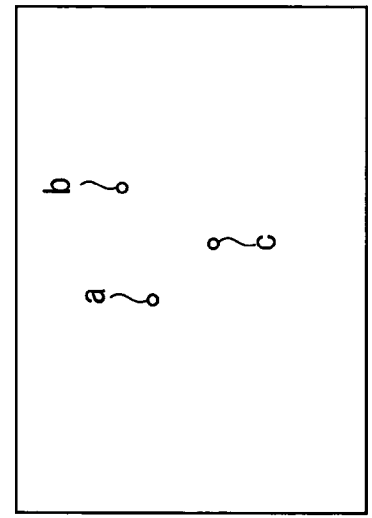
FIG. 4A is a schematic view showing three characteristic points.
Figure 4C:
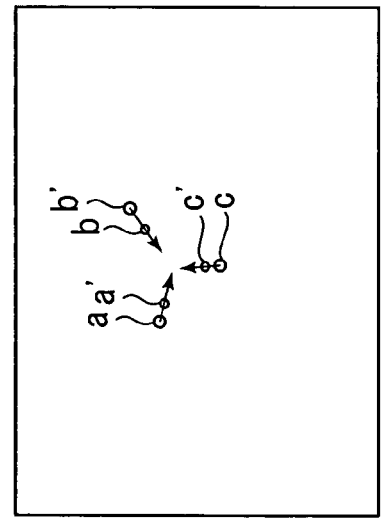
FIG. 4C is a schematic view showing three converging characteristic points.

FIG. 4B shows diverging optical flows, FIG. 4C shows converging optical flows and FIG. 4D shows the optical flows which neither converge nor diverge (but move), for three characteristic points a, b, c shown in FIG. 4A. When the optical flows diverge, the apparatus is moved close to the object and when the optical flows converge, the apparatus is moved away from the object. In this embodiment, the optical flows are in terms of vector values.

A magnitude L of the optical flows is an average of the magnitudes of the vectors. When the flow magnitude L is small, a slight movement at the front end of the fiber occurs and, hence, it can be considered that an operator wants to observe the object carefully. Only in such a case, it is judged whether the optical system is moving slowly close to or away from the object or neither close to nor away from the object. If it is judged that the optical system neither moves away from nor close to the object, no focusing operation is carried out.

For example, a gradient method or a block matching method can be used for the calculation (presumption) of the optical flows. In this embodiment, the gradient method is used.

The pan-focus state of the image pickup optical system 3 and the image pickup device 3c corresponds to the farthermost focus state in which the image pickup device 3c is most advanced. In the case that the optical flows diverge, the distance between the image pickup optical system 3 and the object is reduced. When the optical flows converge, the distance between the image pickup optical system 3 and the object is increased.

Figure 5:
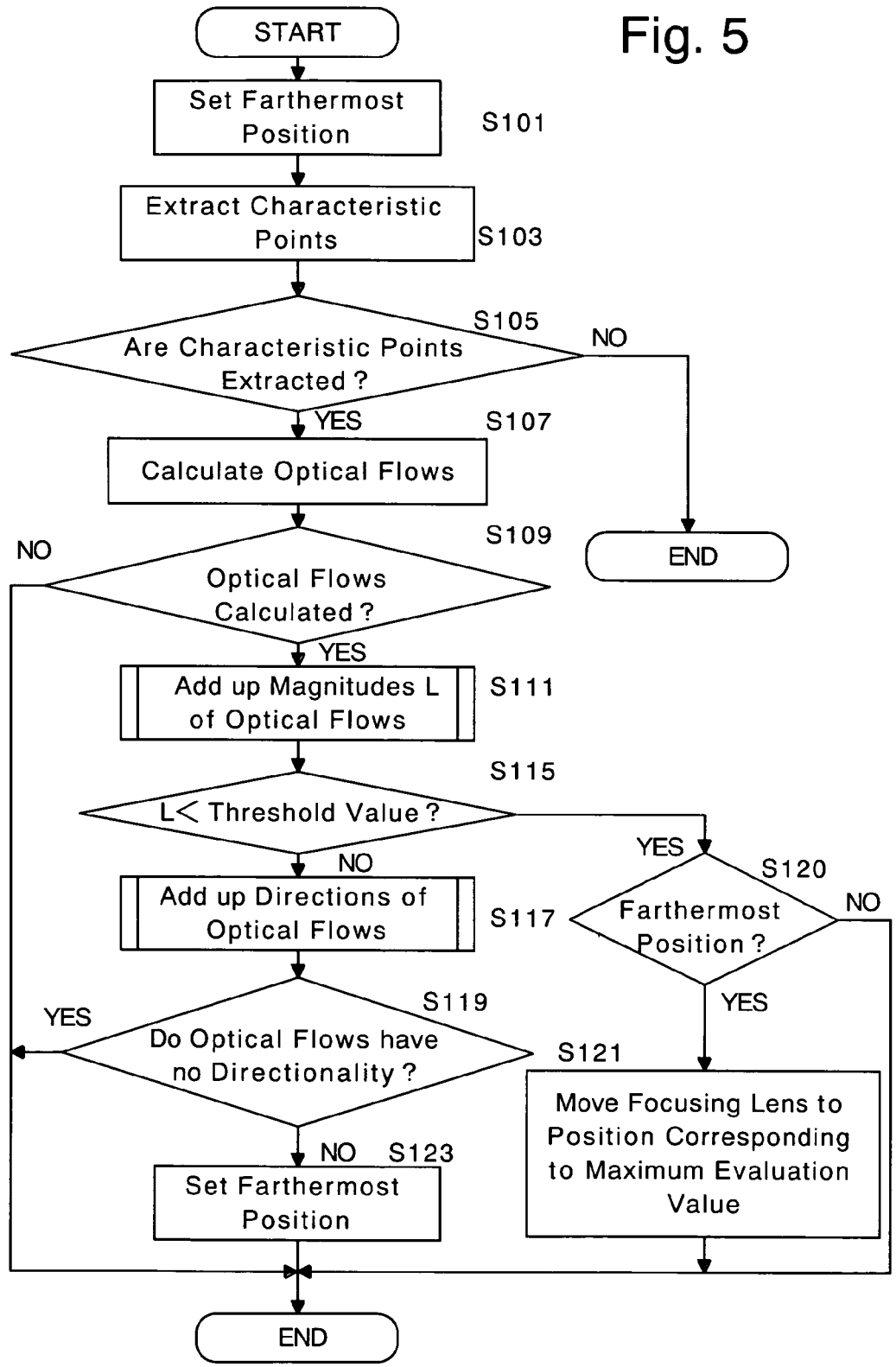
FIG. 5 is a main flow chart of a focusing operation of an automatic focusing apparatus, according to the present invention.
Figure 6:
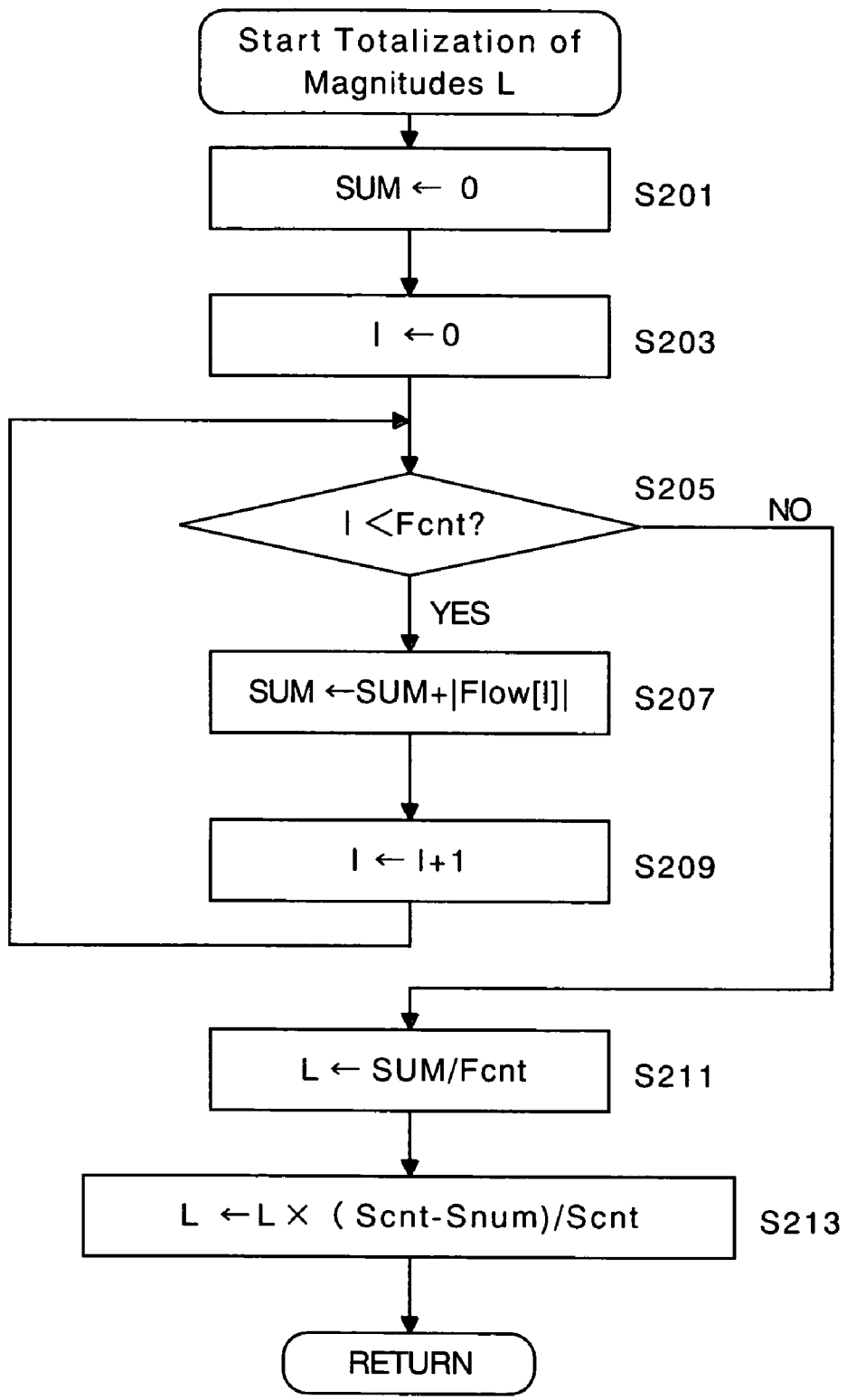
FIG. 6 is a flow chart of an optical flow magnification totalization operation in a focusing operation of an automatic focusing apparatus of the present invention.
Figure 7:
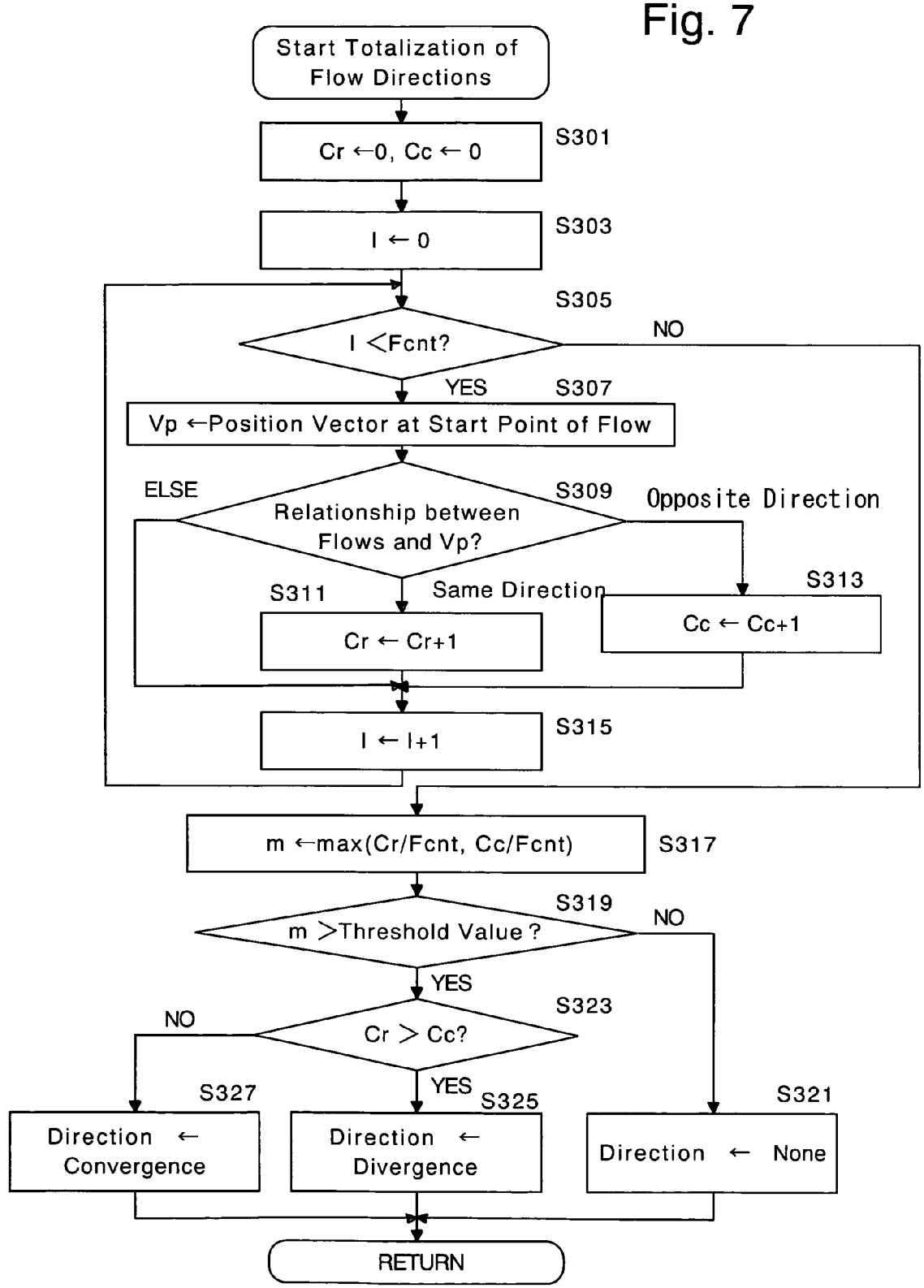
FIG. 7 is a flow chart of an optical flow direction totalization operation in a focusing operation of an automatic focusing apparatus of the present invention.

FIGS. 5 to 7 show flow charts of the control operation of the system controller 11. The system controller 11 reads the image data written in the image memory 7, extracts the characteristic points, calculates the optical flows thereof and adds up the magnitudes L and directions thereof, etc.

FIG. 5 shows a main flow chart of the optical flow calculation. This operation is intermittently repeated at predetermined time intervals.

When the automatic focusing apparatus is activated, the control enters the main routine. The image pickup optical system 3 is set to the farthermost focus state (S101). In the case of the electronic endoscope of the embodiment, the image pickup device 3c is moved to the initial position. In the initial position, the drive force of the stepping motor 4 is released. In the second and subsequent operations, the control skips steps S101 to S103.

Thereafter, characteristic points are extracted from the image signal in one image plane (one frame or one field) obtained (S103). The characteristic points are extracted from, for example, points or contours at which the contrast of the image elements suddenly changes in the vertical, lateral or oblique direction. If no, characteristic point is extracted, the control ends (S105; N, END). Namely, if no characteristic point is extracted, the movable lens system 3b is not moved and the current focus state is maintained.

It is possible to repeat the operations to obtain characteristic points each time the image signals for one image plane are output, until characteristic points are extracted.

When characteristic points are obtained (S105; Y), optical flows are calculated for the characteristic points (S107). In general, the optical flows are calculated from the image signals for two or more image planes.

If no optical flow is obtained, the control ends (S109; N, END). If optical flows are obtained, the following operations are performed (S109; Y).

The magnitudes L of the optical flows are totalized (S111). If the magnitude L of the optical flows is less than a predetermined threshold value, a check is made to determine whether the image pickup optical system 3 is in the farthermost position. If the image pickup optical system 3 is in the farthermost position, the focusing lens group (movable lens system 3b) is moved to a position in which the evaluation value is maximum (S115; Y, S120; Y) and the control ends (S121). If the image pickup optical system 3 is not in the farthermost position (S115; Y, S120; N), no movement of the movable lens system 3b occurs. If the optical flows are reduced at the farthermost position, the movement of the front end of the fiber is small and, hence, the operator needs to perform an AF operation. If the optical flows are reduced at a position other than the farthermost position, an AF operation is being performed.

Note that the totalization of the magnitudes L of the optical flows is an operation to calculate the average of the absolute values thereof. If the magnitude of the optical flows is below a threshold value, it is assumed that the object hardly moves.

If the magnitude of the optical flows is equal to or greater than the threshold value, the directions of the optical flows are added up (S117).

The totalization of the optical flow direction is an operation which counts the number of the vectors whose direction is oriented to the center and the vectors whose direction is oriented away from the center.

If the optical flows have no direction (convergence or divergence), the control ends (S119; Y). If the optical flows have directions, i.e., if the optical flows converge or diverge (S119; N), the movable lens system 3b is set at the farthermost position and the control is returned (S123). For example, when the object moves in a direction perpendicular to the optical axis, the optical flow has no direction.

In the operations mentioned above, if the object moves closer or farther, the movable lens system 3b is moved to a focal position at which the evaluation value is maximum. However, if no characteristic point is extracted, i.e., for example, if almost no contrast exists or the movement is too quickly to obtain characteristic points, the movable lens system 3b is not moved. Furthermore, if the optical flows converge or diverge, and if the magnitudes thereof is smaller than a predetermined threshold value, i.e., if the distance from the object is varied in the optical axis direction, the movable lens system 3b is moved to the focal position in which the evaluation value is maximum.

If the magnitude of the optical flows is above the threshold value and if neither convergence thereof nor divergence occurs, the movable lens system 3b is not moved while it is judged that the object is moved too quickly to carry out the focusing operation.

The details of the totalization of the magnitudes L of the optical flows at S111 will be discussed with reference to a flow chart shown in FIG. 6.

In the totalization operation, the variable SUM is set to 0, i.e., the variable SUM is cleared (S201), and the variable I is set to 0, i.e., the variable I is cleared. The variable SUM represents the sum of the magnitudes L of the optical flows and the variable I represents the number of repetitions. After the variables SUM and I are cleared, operations S205 to S209 are repeated until the variable I is equal to the number of the optical flows Fcnt. At step S205, whether the variable I is smaller than the optical flow number Fcnt is checked. If the variable I is smaller than the number Fcnt, the variable SUM is replaced with the variable SUM plus the magnitude of the Ith optical flow Flow[I] (S205; Y, S207). Moreover, the variable I is replaced with the variable I plus 1 (S209). Note that the symbol [ ] of the Flow[I] is an affix of an array and is not a sum of the vectors but a sum of the magnitudes of the vectors.

If the variable I is not less than the optical flow number Fcnt, i.e., if all of the optical flows in one image plane are added up, the control ends (S205; N, S211). At S211, the value obtained by dividing the variable SUM by the optical flow number Fcnt is substituted for the magnitudes L of the optical flows. Thereafter, the value obtained by the formula: L×(Scnt−Snum)/Scnt, is substituted for the magnitudes L and control is returned (S213; RETURN). Scnt represents the total number of steps necessary for moving the movable lens system 3b from the farthermost position to the closest position and Snum represents the number of steps for moving the movable lens system 3b from the farthermost position. The formula mentioned above defines a weight which makes it possible to evaluate the magnitudes L of the optical flows with the same reference, regardless of the object distance, because the magnitude of the optical flows is enhanced even by a slight relative movement of the object and the front end of the endoscope, when the object distance is reduced.

The details of the totalization of the optical flow direction at step S117 will be discussed with reference to a flow chart shown in FIG. 7. The totalization of the optical flow directions in this embodiment is an operation to count the number of vectors whose direction is oriented toward the center and the vectors whose direction is oriented away from the center, wherein the optical flows are vectors and the direction of the vectors are represented as coordinates for each characteristic point having an origin at the center of the image.

In this flow chart, the divergence variable Cr and the convergence variable Cc are cleared (S301) and the variable I is cleared (S303). The divergence variable Cr represents the sum of the diverging optical flows and the convergence variable Cc represents the sum of the converging optical flows. The operations of steps S305 to S315 are repeated until the variable I exceeds the optical flow number Fcnt, i.e., by the optical flow number Fcnt.

At step S305, it is checked whether or not the variable I is less than the optical flow number Fcnt. If the variable I is less than the optical flow number Fcnt, the control proceeds to step S307 (S305; Y, S307). If the variable I is not less than the optical flow number Fcnt, the control jumps to step S317 (S305; N, S317). If the variable I is less than the optical flow number Fcnt (S305; Y), the vector Vp is substituted by a position vector at the starting point of the optical flow (S307). The vectors Vp extend in a direction from the origin to each starting point of each optical flow. Thereafter, the relationship between the optical flow and the vector Vp is checked (S309). If the directions are identical, the divergence variable Cr is incremented and control proceeds to step S315 (S309; same direction, S311, S315). If the directions are opposite to each other, the convergence variable Cc is incremented, and control proceeds to step S315 (S309; opposite direction, S313, S315). If the directions are neither identical nor opposite, the control proceeds to step S315 (S309; ELSE, S315). At step S315, the variable I is incremented and control is returned to S305.

The operations of steps S305 through S315 are repeated by the number Fcnt of the optical flows, so that whether the optical flows diverge or converge or neither converge nor diverge is determined. If the optical flows diverge, the optical object is relatively moving closer, and if the optical flows converge, the object is relatively moving away. If the optical flows neither converge nor diverge, the object is not moving or is moving in a direction substantially perpendicular to the optical axis.

When the operations of steps S305 through S315 are repeated by the number Fcnt of the optical flows, control proceeds to step S317 (S305; N, S317). At step S317, the formula m=max (Cr/Fcnt, Cc/Fcnt) is calculated. Namely, the variable m is substituted by a mean value of the divergence variables Cr or a mean value of the convergence variables Cc, whichever is larger. Whether or not the variable m is above a predetermined threshold value is checked (S319). If the variable m is not greater than the threshold value, i.e., if the change in the object distance is small, the direction is set to be non-directional and control is returned (S319; N, S321, RETURN).

If the variable m is greater than the threshold value, whether or not the divergence variable Cr is larger than the convergence variable Cc is checked (S319; Y, S323). If the divergence variable Cr is larger than the convergence variable Cc, the direction is judged to be divergent, and control is returned (S323; Y, S325, RETURN). If the convergence variable Cc is (equal to or) larger than the divergence variable Cr, the direction is set to be convergence, and the control is returned (S323; N, S327, RETURN).

Thus, the direction of the optical flows is determined by the totalization operation of the optical flow directions. At step S121, the stepping motor 4 is driven by the automatic focusing unit 15 through the stepping motor driving circuit 21 to thereby move the movable lens system 3b in a direction corresponding to the directionality of the optical flows and obtain an evaluation value. The stepping motor 4 is stopped at a focal position at which the evaluation value is maximum.

As can be understood from the foregoing, in an embodiment of an electronic endoscope apparatus according to the present invention, the optical flows are obtained, based on the picked-up image signals, and if the object is relatively moving closer or farther, the focus is controlled in accordance with the direction of the relative movement of the object. Therefore, no useless focusing operation is carried out. Furthermore, as the focus is controlled in the correct direction, the focusing operation can be carried out within a short space of time, so that a clear image can be smoothly obtained.

As can be understood from the above discussion, since whether or not the focusing device is to be driven is determined in accordance with the average magnitude of the optical flows based upon the image signals of the picked-up image, for a plurality of characteristic points in the illustrated embodiment, a change of the object distance is detected and whether or not the focusing on the object is possible can be judged. If the object can be focused, the focusing device is driven only when it is necessary. Therefore, in an electronic endoscope according to the present invention, the focusing device is automatically activated at appropriate timing without manually operating the focusing device during use of the electronic endoscope, whereby a clear and natural image can be obtained as a result of the automatic and smooth focusing operation.

A second embodiment of the present invention will be discussed below. In the second embodiment, the image pickup optical system 3 is normally maintained in a pan-focus state and the optical flows are measured based on the picked-up images. If the optical flows of the characteristic points diverge, the focusing is carried out for the short object distance. If the optical flows converge, the focusing is carried out for the long object distance. If the optical flows of the characteristic points neither converge nor diverge or if the magnitude of the optical flows is small even if the optical flows converge or diverge, no focusing operation is carried out.

Figure 8:
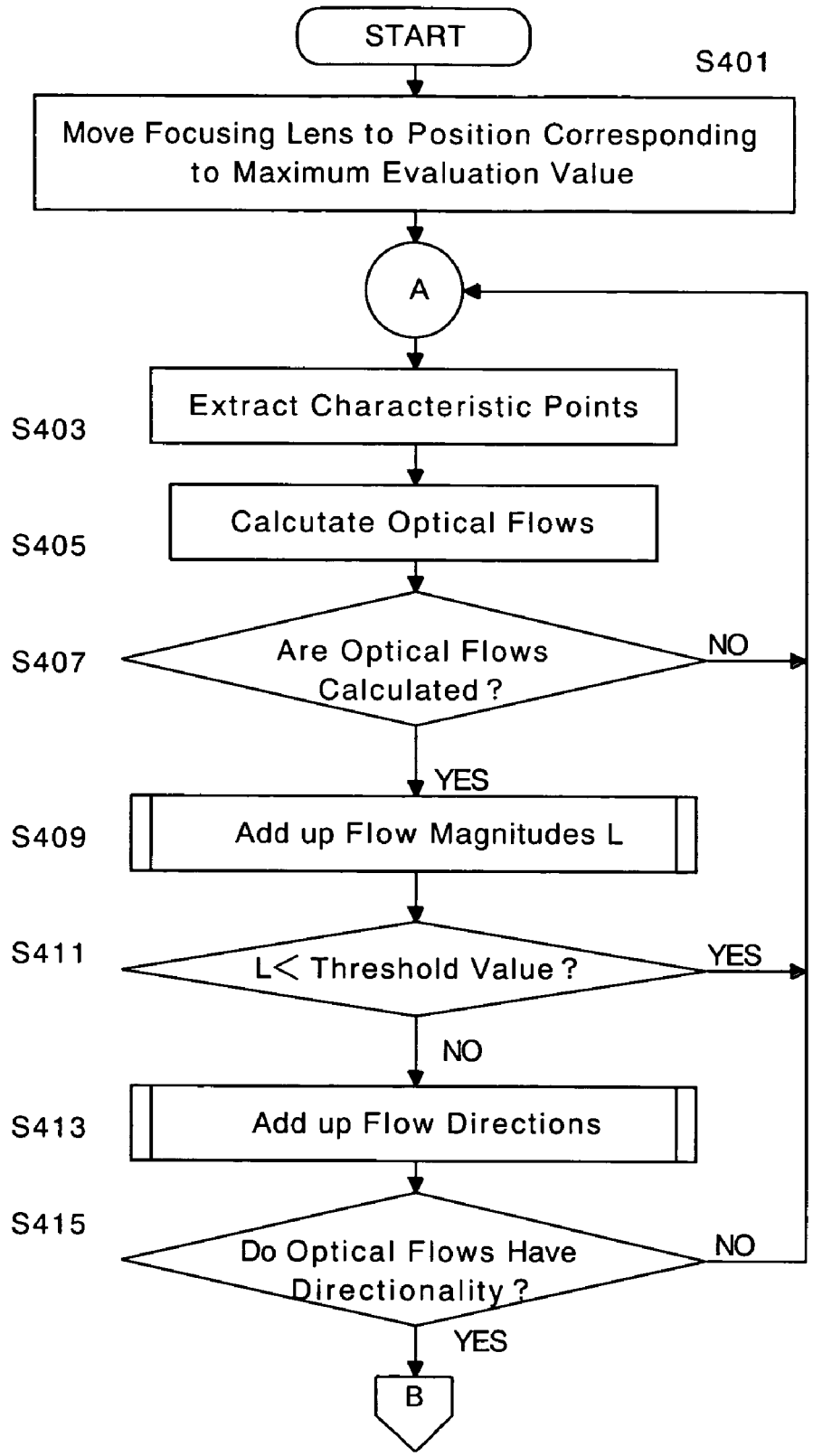
FIG. 8 shows a first portion of a main flow chart of an automatic focusing operation of an automatic focusing apparatus according to a second embodiment of the present invention.
Figure 9:
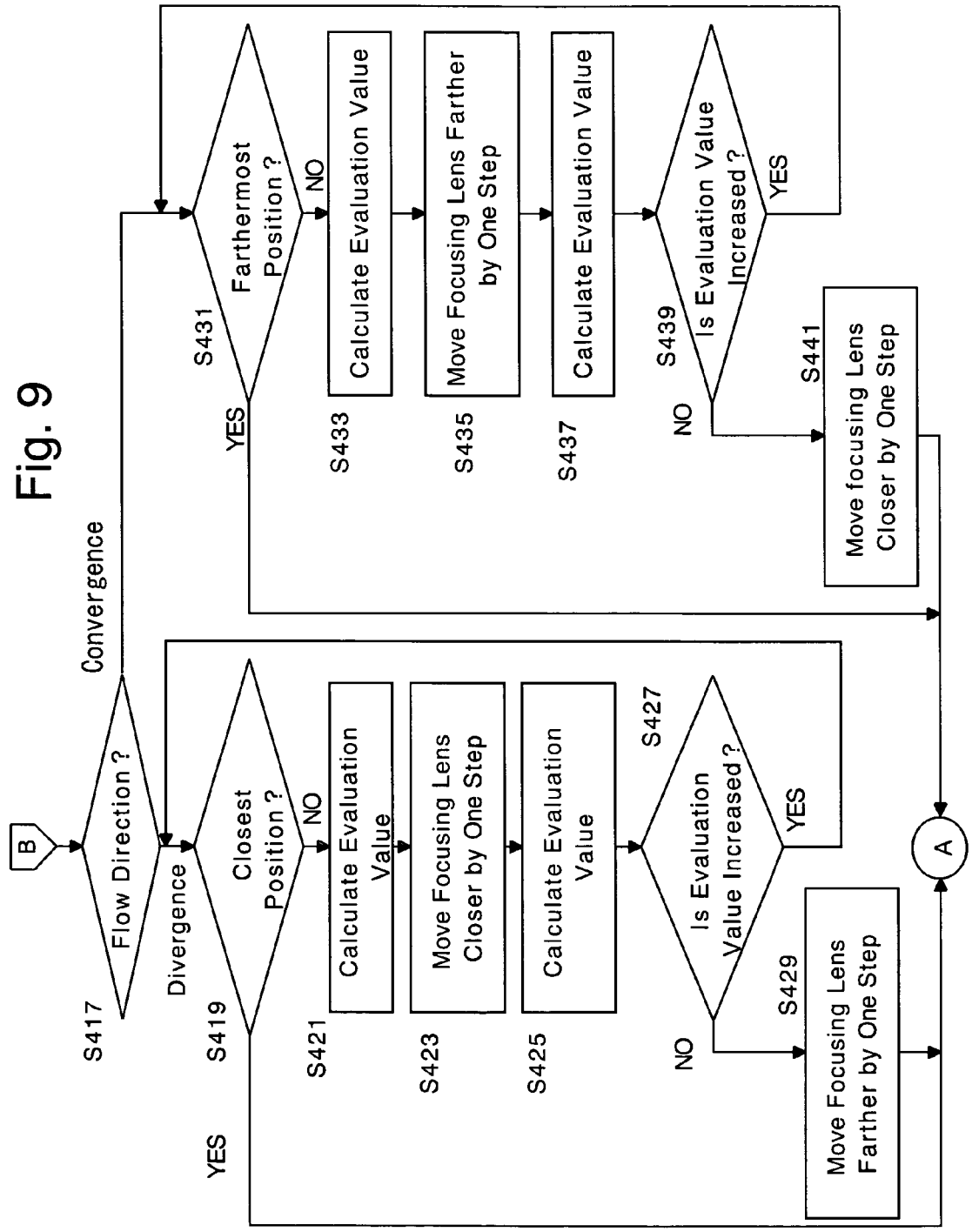
FIG. 9 shows a second portion of a main flow chart of an automatic focusing operation of an automatic focusing apparatus according to a second embodiment of the present invention.

FIGS. 8 through 9 show the operations which are controlled by the system controller 11. FIG. 8 shows a main flow chart of the optical flow calculation operation. This operation is repeatedly performed while the automatic focusing device is activated.

In the main flow chart, the evaluation value is obtained based on the image signals output from the image pickup device 3c and the focusing is carried out so that the evaluation value becomes maximum (S401). This is an initial focus control and is carried out only once at the commencement of the operation.

Thereafter, the luminance signal is extracted from the image signals for one image plane (one frame or field), output from the image pickup device 3c to thereby extract the characteristic points in the image plane (S403). The characteristic points are extracted from, for example, points or contours at which the contrast of the image elements suddenly changes in the vertical or lateral or oblique direction.

When the characteristic points are obtained, optical flows are calculated for the characteristic points (S405). The optical flows are calculated from the image signals for two or more image planes.

If no optical flow is obtained, control is returned to step S403 and the operations beginning with step S403 are repeated (S407; N, S403). If optical flows are obtained, the magnitudes L of the optical flows are totalized (S407; Y, S409). If the totalized magnitude L of the optical flows is less than a predetermined threshold value, the control is returned to S403 to repeat the operations following S403 (S411; Y, S403).

Note that the totalization of the magnitudes L of the optical flows is an operation to calculate the average of the absolute values thereof. If the magnitude of the optical flows is below a threshold value, it is assumed that the object hardly moves.

If the magnitude of the optical flows is above the threshold value, the directions of the optical flows are added up (S411; N, S413). The totalization of the optical flow directions is an operation to count the number of vectors whose direction is oriented to the center and vectors whose direction is oriented away from the center.

If the optical flows have no directionality, control is returned to step S403 to repeat the operations following step S403 (S415; N, S403). For example, when the object moves in a direction perpendicular to the optical axis, the optical flow is non-directional. If the optical flows are directional, i.e., if the optical flows converge or diverge (S415; Y), control proceeds to step S417 shown in FIG. 9. At S417, the direction of the optical flows is judged.

<Divergence of Optical Flows>

If it is judged that the optical flows diverge, i.e., if the optical system is close to the object (S417; divergence), the following operations are carried out.

Whether or not the movable lens system 3b is in the closest position is checked (S419). If the movable lens system 3b is closest to the object, the control is returned to S403 (S419; Y, S403). This is because no further movement of the movable lens system 3b toward the object is possible.

If the movable lens system 3b is not located at the closest position, the evaluation value is calculated and the movable lens system 3b is moved by one step toward the closest position (S419; N, S421; S423). Thereafter, the evaluation value is calculated and whether or not the evaluation value has been increased is checked (S425, S427). If there is an increase of the evaluation value, the control is returned to S419 to repeat the operations subsequent to S419 (S427; Y, S419). An increase of the evaluation value means that the movable lens system 3b has been moved toward the focal position, but whether or not the object is in-focus is indefinite. If there is no increase in the evaluation value, the movable lens system 3b is moved by one step toward the far-point focus side and the control is returned to S403 (S427; N, S429, S403).

Thus, if the optical flows diverge, the movable lens system 3b is moved toward the focal point of the short object distance, so that the optical system can be quickly focused on the object.

<Convergence of Optical Flows>

If it is detected in the optical flow direction judgment that the optical flows converge, the following operations are carried out (S417; convergence).

Whether or not the movable lens system 3b is located at the farthermost point is checked (S431). If the movable lens system 3b is in the farthermost point, the control is returned to S403 (S431; Y, S403), because no further movement of the movable lens system toward the focal point of the long object distance can occur.

If the movable lens system 3b is not located at the farthermost point, the evaluation value is calculated and the movable lens system 3b is moved by one step toward the far-point side (S431; N, S433, S435). Thereafter, the evaluation value is calculated and whether or not the evaluation value has been increased is checked (S437, S439). If there is an increase of the evaluation value, the control is returned to S431 to repeat the operations subsequent to S431 (S439; Y, S431). An increase of the evaluation value means that the movable lens system has been moved toward the focal position, but whether or not the object is in-focus is indefinite. If there is no increase in the evaluation value, the movable lens system is moved by one step toward the near-point focus side and the control is returned to S403 (S439; N, S441, S403). Thus, if the optical flows converge, the movable lens system 3b is moved toward the focal point of the long object distance, so that the optical system can be quickly focused on the object.

By repeating the operations mentioned above, the optical flows are detected from the picked-up images and the focusing operation is carried out when the optical flows converge or diverge and when the magnitude of the optical flows is above a predetermined value. Consequently, the focusing operation can be smoothly carried out and a clear and natural image can be obtained.

The details of the totalization of the magnitudes L of the optical flows at step S409 are the same as shown in FIG. 7.

The totalization operation of the optical flow directions is the same as that of the flow chart shown in FIG. 7. Namely, the totalization of the optical flow directions in this embodiment is an operation to count the number of vectors whose direction is oriented toward the center and the vectors whose direction is oriented away from the center, in terms of the coordinate whose origin is defined by the center of the image for each characteristic point wherein the optical flows are represented by vectors whose direction is represented by the coordinate.

Thus, the direction of the optical flows is determined by the totalization operation of the optical flow directions. At steps S423 or S425, the stepping motor 4 is driven by the automatic focusing unit 15 via the stepping motor driving circuit 21 to thereby move the movable lens system 3b in a direction corresponding to the directionality of the optical flows and obtain an evaluation value. The stepping motor 4 is stopped at a focal position in which the evaluation value is maximum.

Although the image pickup optical system has a short focal length in the embodiment mentioned above, the present invention can be applied to a zoom lens. In an application to a zoom lens, as the optical flows diverge and converge in a zoomed-in position and in a zoomed-out position, respectively, this fact is considered when the judgment is made or those next to the optical flows are excluded during the zooming operation. Moreover, although the above embodiment has been applied to an endoscope apparatus for medical use, the present invention is not limited thereto and can be equally applied to an industrial endoscope apparatus having like function.

As can be understood from the above discussion, in an electronic endoscope according to the present invention, the focusing device is automatically activated to move toward the short object distance side and the long object distance side when the optical flows totalized in accordance with the picked-up image signals, for a plurality of characteristic points obtained, diverge and converge, respectively. Accordingly, according to the present invention, the focusing can be carried out in a correct direction in accordance with the object distance.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An automatic focusing apparatus of an endoscope comprising:
   an image pickup optical system comprising a stationary lens system, a movable lens system and an image pickup device for converting an optical image into an electric image signal, at a predetermined cycle and outputting the electric signal, wherein the stationary lens system, the movable lens system and the image pickup device are arranged in this order from an object;
   a focusing device;
   an optical flow calculation device for calculating optical flows in accordance with said image signals in a first image plane at a first time and in a second image plane at a second time, said second time being different from said first time, and for calculating an average of magnitudes and directions of said optical flows; and
   a judgment device for determining whether or not the focusing device is to be driven in accordance with said calculated average of magnitudes and directions of said optical flows,
   wherein said optical flow calculation device is further configured to total the magnitude of said optical flows after said calculations, and to weigh the magnitude of said optical flows by the flowing relationship:

$L \times (Scnt - Snum)/Scnt$ wherein
   L designates the magnitude of said optical flows:
   Scnt designates the total number of drive steps necessary for moving the movable lens system from a furthest position to a closest position; and
   Snum designates the number of drive steps necessary for moving the movable lens system from the furthest position to a present position.

2. The automatic focusing apparatus according to claim 1, further comprising a signal separating device for separating luminance signals from image signals supplied by the image pickup device, wherein said optical flow calculation device calculates optical flows in accordance with said luminance signals.

3. The automatic focusing apparatus according to claim 2, wherein said optical flow calculation device detects a plurality of characteristic points, based on said luminance signals of said first image plane and said second image plane, and calculates said optical flows based on the characteristic points in the first image plane and the characteristic points in the second image plane.

4. The automatic focusing apparatus according to claim 1, wherein said judgment device determines that the focusing device is not driven when the optical flow calculation device fails to calculate said average of said magnitude and said direction of each optical flow.

5. The automatic focusing apparatus according to claim 4, wherein said image pickup optical system comprises a focusing optical system which is moved along an optical axis to perform a focusing operation, the focusing optical system comprising the movable lens system, and wherein said focusing device comprises a drive device for moving the focusing optical system and a focus detection device for detecting a focus state in accordance with the image signals output from the image pickup device.

6. The automatic focusing apparatus according to claim 5, further comprising a power varying device for varying the optical power of said focusing optical system by moving said focusing optical system in the optical axis direction.

7. The automatic focusing apparatus according to claim 5, wherein said focus detection device detects the focus state by detecting a contrast based on said image signals.

8. The automatic focusing apparatus according to claim 5, wherein said focusing optical system is normally located in a pan-focus position and said judgment device activates the focusing device when the average of the magnitudes of the optical flows is below a predetermined value.

9. The automatic focusing apparatus according to claim 5, wherein said optical flow calculation device weights the magnitudes of the optical flows in accordance with the position of the focusing optical system in the optical axis direction.

\* \* \* \* \*